(12) United States Patent
Wagner (10) Patent No.: US 6,221,855 B1
(45) Date of Patent: Apr. 24, 2001

(54) REGULATION OF NUCLEIC ACID EXPRESSION BY HEPARAN SULFATE AND BIOLOGICAL EQUIVALENTS THEREOF

(75) Inventor: William D. Wagner, Clemmons, NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 09/266,258

(22) Filed: Mar. 11, 1999

(51) Int. Cl.[7] ............................. A01N 43/04; A01N 43/72
(52) U.S. Cl. ................................. 514/56; 536/21
(58) Field of Search ................... 514/56; 536/21

(56) References Cited

U.S. PATENT DOCUMENTS

| | | |
|---|---|---|
| 4,160,452 | 7/1979 | Theeuwes . |
| 4,256,109 | 3/1981 | Theeuwes . |
| 4,265,874 | 5/1981 | Bonsen et al. . |
| 5,461,029 | 10/1995 | Backer et al. . |

OTHER PUBLICATIONS

Au et al., 1993, Haemostasis 23:177–182.
Bortoff and Wagner, 1995, Mol. Cell. Biol. 6:13.
Boyle and Compton, 1998, J. Virol. 72:1826–1833.
Carey, 1997, J. Biochem. 327:1–16.
Castellot et al., 1989, J. Cell Biol. 109:3147–3155.
Chen et al., 1997, Nature Medicine 3:866–871.
Ficker et al., 1990, J. Biol. Chem. 265:2476–2482.
He et al., 1995, Nature Lett. 378:92–96.
Herold et al., 1997, Antimicrob. Agents Chemother. 41:2776–2780.
Immergluck et al., 1998, J. Gen. Virol. 79:549–559.
Jackson et al., 1996, J. Virol. 70:5282–5287.
Klimstra et al., 1998, J. Virol. 72:7357–7366.
Kuroki et al., 1995, J. Biol. Chem. 270:15022–15028.
Layne et al., 1998, J. Biol. Chem. 273:15654–15660.
Li et al., 1995, J. Virol. 69:4758–4768.
Maccarana et al., 1993, J. Biol. Chem. 268:23898–23905.
Majack et al., Proc. Natl. Acad. Sci. USA 83:9050–9054.
McGwire et al., 1997, Life Sciences 60:715–724.
Monreal et al., 1993, Haemostasis 23:179–183.
Ohno et al., 1996, 1996, Biochim. Biophys. Res. Commun. 228:411–414.
Pukac et al., 1990, Cell Regulation, 1:435–443.
Reilly et al., 1987, J. Cell. Physiol. 131:149–157.
Reilly et al., 1988, J. Cell. Physiol. 136:23–32.
Reilly et al., 1989, J. Biol. Chem. 264:6990–6995.
Saksela et al., 1988, J. of Cell Biology 107:743–751.
Settle et al., 1995, Proc. Natl. Acad. Sci. USA 92:9470–9474.
Skidgel et al., 1988, Trends Pharmacol. Sci. 9:299–304.
Smith et al., 1979, Exp. Mol. Pathol. 30:190–208.
Song and Fricker, 1996, J. Biol. Chem. 270:25007–25013.
Song and Fricker, 1996, J. Biol. Chem. 271:2884–2889.
Summerford and Samulski, 1998, J. Virol. 72:1438–1445.
Trybala et al., 1998, J. Biol. Chem. 273:5047–5052.
Weiser et al., 1997, Mol. Biol. Cell 8:999–1011.
Xin et al., 1997, DNA and Cell. Biol. 16:897–909.
Breiner et al., Journal of Virology, 72(10):8098–8104, Oct. 1999.*
Wagner et al., The FASEB Jurnal, 12(5):4096, Mar. 1998.*

* cited by examiner

*Primary Examiner*—Brenda Brumback
(74) *Attorney, Agent, or Firm*—Morgan, Lewis & Bockius LLP (57) ABSTRACT

The present invention relates to the use of heparan sulfate, or a biological equivalent thereof, to regulate nucleic acid expression, expression of cell receptors, and infection by hepatitis B virus.

13 Claims, 1 Drawing Sheet

FIG. 1

SEQUENCE LISTING

```
<160> NUMBER OF SEQ ID NOS: 6

<210> SEQ ID NO 1
<211> LENGTH: 147
<212> TYPE: PRT
<213> ORGANISM: Columba sp.
<220> FEATURE:
<223> OTHER INFORMATION: portion of pigeon gp180 sequence

<400> SEQUENCE: 1

Met Leu Val Glu Val His Lys Gly Val His Gly Phe Val Gln Asp Lys
 1               5                  10                  15

Ser Gly Lys Ala Ile Ser Lys Ala Thr Ile Val Leu Asn Asp Ser Leu
            20                  25                  30

Arg Val Tyr Thr Lys Glu Gly Gly Tyr Phe His Val Leu Leu Ala Pro
        35                  40                  45

Gly Leu His Asn Ile Asn Ala Ile Ala Asp Gly Tyr Gln Gln Lys His
    50                  55                  60

Val Lys Val Leu Val Arg His Asp Ala Pro Ser Ser Val Phe Ile Val
65                  70                  75                  80
```

-continued

```
Phe Asp Thr Glu Asn Arg Ile Phe Gly Leu Pro Arg Glu Leu Val Val
             85                  90                  95

Thr Val Ala Gly Ala Ser Met Ser Ala Leu Val Leu Thr Ala Cys Ile
            100                 105                 110

Ile Trp Cys Val Cys Ser Ile Lys Ser Asn Arg His Lys Asp Gly Phe
        115                 120                 125

His Arg Leu Arg Gln His His Asp Asp Tyr Glu Asp Glu Ile Arg Met
130                 135                 140

Met Ser Thr
145

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Forward PCR
      primer (P3) for pigeon gp180

<400> SEQUENCE: 2
attaaccctc actaaatgct ggtgg                                             25

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Reverse PCR
      primer (T2) for pigeon gp180

<400> SEQUENCE: 3
cattatgctg agtgatatct tttttttttac                                       30

<210> SEQ ID NO 4
<211> LENGTH: 147
<212> TYPE: PRT
<213> ORGANISM: Anas sp.
<220> FEATURE:
<223> OTHER INFORMATION: Portion of Duck gp180

<400> SEQUENCE: 4

Met Leu Val Glu Val His Lys Gly Val His Gly Phe Val Gln Asp Lys
  1               5                  10                  15

Ser Gly Lys Ala Ile Ser Lys Ala Thr Ile Val Leu Asn Glu Gly Leu
             20                  25                  30

Arg Val Tyr Thr Lys Glu Gly Gly Tyr Phe His Val Leu Leu Ala Pro
         35                  40                  45

Gly Leu His Asn Ile Asn Ala Ile Ala Asp Gly Tyr Gln Gln Lys His
     50                  55                  60

Met Lys Val Leu Val Arg His Asp Ala Pro Ser Ser Val Phe Ile Val
 65                  70                  75                  80

Phe Asp Met Glu Asn Arg Ile Phe Gly Leu Pro Arg Glu Leu Val Val
                 85                  90                  95

Thr Val Ala Gly Ala Ser Met Ser Ala Leu Val Leu Thr Ala Cys Ile
            100                 105                 110

Ile Trp Cys Val Cys Ser Ile Lys Ser Asn Arg His Lys Asp Gly Phe
        115                 120                 125
```

```
Pro Thr Leu Arg Gln His His Asp Asp Tyr Glu Asp Glu Ile Arg Met
    130                 135                 140

Met Ser Thr
145

<210> SEQ ID NO 5
<211> LENGTH: 147
<212> TYPE: PRT
<213> ORGANISM: Rattus sp.
<220> FEATURE:
<223> OTHER INFORMATION: Portion of rat carboxypeptidase D

<400> SEQUENCE: 5

Met Leu Val Glu Val His Lys Gly Val His Gly Leu Val Lys Asp Lys
  1               5                  10                  15

Thr Gly Lys Pro Ile Ser Lys Ala Val Ile Val Leu Asn Glu Gly Ile
             20                  25                  30

Arg Val His Thr Lys Glu Gly Gly Tyr Phe His Val Leu Leu Ala Pro
         35                  40                  45

Gly Val His Asn Ile Asn Ala Ile Ala Asp Gly Tyr Gln Gln Gln His
     50                  55                  60

Ser Gln Val Phe Val Arg His Asp Ala Ala Ser Ser Val Phe Ile Val
 65                  70                  75                  80

Val Asp Thr Asp Asn Arg Ile Phe Gly Leu Pro Arg Glu Leu Val Val
                 85                  90                  95

Thr Val Ser Gly Ala Thr Met Ser Ala Leu Ile Leu Thr Ala Cys Ile
            100                 105                 110

Ile Trp Cys Ile Cys Ser Ile Lys Ser Asn Arg His Lys Asp Gly Phe
        115                 120                 125

His Arg Leu Arg Gln His His Asp Asp Tyr Glu Asp Glu Ile Arg Met
    130                 135                 140

Met Ser Thr
145

<210> SEQ ID NO 6
<211> LENGTH: 147
<212> TYPE: PRT
<213> ORGANISM: Homo sapiens
<220> FEATURE:
<223> OTHER INFORMATION: Portion of human carboxypeptidase D

<400> SEQUENCE: 6

Met Leu Val Glu Val His Lys Gly Val His Gly Phe Val Lys Asp Lys
  1               5                  10                  15

Thr Gly Lys Pro Ile Ser Lys Ala Val Ile Val Leu Asn Glu Gly Ile
             20                  25                  30

Lys Val Gln Thr Lys Glu Gly Gly Tyr Phe His Val Leu Leu Ala Pro
         35                  40                  45

Gly Val His Asn Ile Asn Ala Ile Ala Asp Gly Tyr Gln Gln Lys His
     50                  55                  60

Ser Gln Val Phe Val Arg His Asp Ala Ala Ser Ser Val Phe Ile Val
 65                  70                  75                  80

Val Asp Thr Asp Asn Arg Ile Phe Gly Leu Pro Arg Glu Leu Val Val
                 85                  90                  95

Thr Val Ser Gly Ala Thr Met Ser Ala Leu Ile Leu Thr Ala Cys Ile
            100                 105                 110

Ile Trp Cys Ile Cys Ser Ile Lys Ser Asn Arg His Lys Asp Gly Phe
        115                 120                 125
```

```
His Arg Leu Arg Gln His His Asp Asp Tyr Glu Asp Glu Ile Arg Met
    130                 135                 140

Met Ser Thr
145
```

REGULATION OF NUCLEIC ACID EXPRESSION BY HEPARAN SULFATE AND BIOLOGICAL EQUIVALENTS THEREOF

STATEMENT REGARDING FEDERALLY SPONSORED RESEARCH OR DEVELOPMENT

This invention was supported in part by funds from the U.S. Government (NHLBI Grant No. HL45848 and NRSA Training Grant HL07115) and the U.S. Government may therefore have certain rights in the invention.

BACKGROUND OF THE INVENTION

The present invention relates to regulation of gene expression by heparan sulfate or analogs thereof.

Hepadnaviruses, as typified by human hepatitis B virus, the prototype member of this virus family, are small enveloped DNA viruses that produce persistent infections of liver cells and cause acute and chronic hepatitis (Kuroki et al., 1995, J. Biol. Chem. 270:15022–15028). Until recently, the process by which hepatitis B virus particles entered host cells was poorly understood. However, the prior art teaches that human hepatitis B virus binds to cells via a cell receptor protein, i.e., carboxypeptidase D (CPD) which is the human homolog of duck glycoprotein 180 (gp180). Duck gp180, which shares approximately 80% amino acid sequence identity with human carboxypeptidase D, has been demonstrated to serve as the hepatitis B virus receptor which mediates viral entry into cells in a duck hepatocyte infection model (Kuroki et al., 1995, J. Biol. Chem. 270:15022–15028).

Carboxypeptidases perform several important functions in a variety of tissues. These proteins may be broadly divided into two groups based on both function and homology (Skidgel, 1988, Trends Pharmacol. Sci. 9:299–304). One group, which consists of proteins typically 30 to 40 kDa in size, includes the digestive enzymes carboxypeptidase A and carboxypeptidase B. The second group, which includes carboxypeptidase D, is a family of regulatory mammalian basic metallocarboxypeptidases related to ancestral digestive pancreatic carboxypeptidase B. These enzymes, which are typically 50 to 60 kDa in size, specifically cleave C-terminal arginine or lysine residues from peptides and proteins (McGwire et al., 1997, Life Sciences 60:715–724).

The basic metallocarboxypeptidases have a variety of functions such as prohormone processing, activation and inactivation of peptide hormones, regulation of plasminogen binding to cells, and even transcriptional regulation. There are a number of members of the basic metallocarboxypeptidases including the secretory vesicle carboxypeptidase E (CPE, also known as carboxypeptidase H), carboxypeptidase N (CPN), and the extracellular membrane-bound carboxypeptidase M (CPM) (Skidgel, 1988, Trends Pharmacol. Sci. 9:299–304).

Carboxypeptidase D, which was recently isolated and characterized from bovine pituitary membranes, is a 180 kDa membrane-associated protein present in both internal and plasma membranes of the cell, and is believed to play a role in processing of proteins that transit the secretory pathway (Song and Fricker, 1996, J. Biol. Chem. 271:28884–28889). The amino-terminal sequence of bovine membrane CPD is very similar to duck glycoprotein 180 (gp180), a protein identified by its ability to bind hepatitis B virus. More recently, CPD has been identified as a membrane-bound CP present in human skin fibroblasts and in the mouse monocyte macrophage cell line J774A.1 (McGwire et al., 1997, Life Sci. 60:715–724). Prior to these studies, it was understood that the only true membrane-bound CP was CPM, although CPE can associate with membranes through an amphipathic carboxy-terminal sequence.

Mouse and human CPD are similar to bovine pituitary tissue CPD. The gene encoding duck gp180 has also been sequenced (Kuroki et al., 1995, J. Biol. Chem. 270:15022–15028). The deduced amino acid sequence of duck gp180 has three CPE-like domains followed by a predicted transmembrane domain and a short cytoplasmic tail. Glycoprotein 180 has been found to have CP activity and an acidic pH optimum. Based on their similar size, pH optima, and amino-terminal sequence, it appears that bovine CPD is a homolog of duck gp180. Further, comparison of amino acid sequences deduced from full-length cDNA clones demonstrates human CPD is 75% and 90% homologous with duck and rat CPD, respectively.

The distribution of soluble, as well as the membrane-bound form of CPD in rat tissues has been found to be more broad than that of CPE, suggesting that CPD and CPE have functions which are distinct from each other (Song and Fricker, 1996, J. Biol. Chem. 271:2884–2889). Soluble CPD activity has been purified to homogeneity and is characterized as two protein bands of approximately 170 kDa and 135 kDa, which are converted to 155 kDa and 115 kDa by treatment with endoglycosidase F (Song and Fricker, 1996, J. Biol. Chem. 271:2884–2889). The N-terminal amino acid sequences of two soluble forms of CPD were identical to one another and to the predicted N-terminal amino acid sequence of duck gp180. The soluble and membrane bound forms of CPD have similar pH optima, inhibitor specificity, and kinetic parameters for substrate hydrolysis. The highest levels of CPD activity were found in pituitary and adrenal glands, and in brain. Western blot analysis indicated that soluble and membrane bound forms of CPD were present in rat brain, heart, liver, and kidney.

Although the removal of carboxy-terminal basic amino acid residues is required for the activity of many neuropeptides, there may be other receptors such as the insulin receptor which require a similar CP action to produce a functional protein. The possibility that CPD is involved in the processing of growth factors and/or growth factor receptors is supported by studies in Drosophila. More specifically, the Drosophila homolog of CPD, the silver gene, is required for viability, development of cuticular structures, and changes in wing differentiation (Settle et al., 1995, Proc. Natl. Acad. Sci. USA 92:9470–9474). These studies suggest a role for CPD in mammalian cell growth and differentiation.

Although the precise function of CPD and duck gp180 in uninfected cells is not known, duck gp180 shares the greatest homology with carboxypeptidase H which is found on the membranes of secretory granules in many endocrine and neuroendocrine cells and is involved in the post-translational maturation of insulin and enkephalin from their precursor polypeptides (Kuroki et al., supra). Further, carboxypeptidase has other ligands, e.g., $CD8^+$, besides hepatitis B virus. Indeed, another gp180 has been identified on the surface of human intestinal mucosal cells. Although not extensively studied to date, this human gp180 is reported to bind $CD8^+$ lymphocytes and may play a role in oral tolerance through an immune suppressor function as suggested by the fact that the level of this gp180 protein is decreased in the mucosal cells of patients with Crohn's disease and with inflammatory bowel disease. Upon treatment with N-glycanase, this gp180 protein, which has not been identified as a CP, migrates at a smaller size on SDS gels than N-glycanase treated CPD. In sum, although carboxypeptidase D, and duck gp180 in avian hepatocytes have been demonstrated to be involved in hepatitis B virus entry into host cells, the normal function of these peptides remains to be elucidated as does the precise mechanism by which these proteins mediate viral entry.

Heparan sulfate proteoglycans have been implicated in virus binding and entry into cells in the case of numerous viruses. See, e.g., Klimstra et al., 1998, J. Virol. 72:7357–7366 (Sindbis virus); Immergluck et al., 1998, J. Gen. Virol. 79:549–559 (herpes simplex virus-1; HSV-1); Trybala et al., 1998, J. Biol. Chem. 273:5047–5052 (pseudorabies virus); Boyle and Compton, 1998, J. Virol. 72:1826–1833 (human cytomegalovirus); Jackson et al., 1996, J. Virol. 70:5282–5287 (foot-and-mouth disease virus); Witrouw and De Clercq, 1997, Gen. Pharmacol. 29:497–511 (human immunodeficiency virus); Chen et al., 1997, Nature Medicine 3:866–871 (dengue virus); Summerford and Samnulski, 1998, J. Virol. 72:1438–1445 (human parvovirus adeno-associated virus type 2); Li et al., 1995, J. Virol. 69:4758–4768 (bovine herpesvirus 1)). In addition, the non-viral human pathogens *Chlamydia trachomatis* and *Neisseria gonorrhoeae*, have also been demonstrated to utilize heparan sulfate proteoglycans in their host cell entry mechanism (Herold et al., 1997, Antimicrob. Agents Chemother. 41:2776–2780).

In all of the afore-mentioned studies, heparan sulfate, or its analog heparin, was shown to exhibit anti-viral activity. However, the mechanism of inhibition of virus infection was determined to occur by a physical blocking of the virus interaction with the cell surface, wherein the heparan sulfate either bound to the cellular heparan sulfate proteoglycan (HSP), or bound to the viral proteins capable of interacting with the HSP. Indeed, two heparin-binding proteins, HBNF and MK, were demonstrated to inhibit HSV-1 infection of cells by inhibiting viral adsorption to the cell surface (U.S. Pat. No. 5,461,029). Therefore, the prior art teaches that heparan sulfate and its analogue heparin block virus infection by inhibiting virus adsorption to the host cell surface, which virus adsorption is mediated by virus binding to cell surface heparan sulfate proteoglycans.

In addition to its anti-viral effects, heparin inhibits vascular smooth muscle cell (SMC) proliferation and migration both in vivo and in vitro (Au et al., 1993, Haemostasis 23:177–182). It is not known how heparin produces these effects. However, it appears that heparin's inhibitory action is probably mediated during the $G_1$ phase of the cell cycle (Au et al., supra, Reilly et al., 1989, J. Biol. Chem. 264:6990–6995). As stated previously herein, the precise mechanism(s) by which heparin inhibits mitogenesis is not known, but heparin has been demonstrated, inter alia, to interfere with various $G_1$ events, decrease the expression of c-myc and c-fos protooncogenes (Pukac et al., 1990, Cell Regulation 1:435–443) as well as the expression of the Oct-1 gene (Weiser et al., 1997, Mol. Biol. Cell 8:999–1011) and the tissue-type plasminogen activator (t-PA) and collagenase (Au et al., 1993, Haemostasis 23:177–182), inhibit a protein kinase C-dependent pathway for mitogenesis (Castellot et al., 1989, J. Cell Biol. 109:3147–3155), and decrease the number of epidermal growth factor (EGF) receptors on the surface of SMCs (Reilly et al., 1987, J. Cell. Physiol. 131:149–157, Reilly et al., 1988, J. Cell. Physiol. 136:23–32). The prior art does not teach how the number of EGF receptors is decreased, the prior art only discloses that heparin reduces their number by 53–60% without a decrease in the affinity of the receptors for EGF. Further, the prior art discloses that EGF inhibits heparin's antiproliferative effect in SMCs while other mitogens have little or no effect in reducing this effect of heparin (Reilly et al., 1988, J. Cell. Physiol. 136:23–32). In sum, heparin exerts an antiproliferative effect on SMCs although the precise mechanism(s) for this effect remains to be elucidated.

There is an acute and unfilled need for the development of antiviral therapeutics which therapeutics regulate expression of cell surface receptor molecules for the regulation of virus infection of cells. There is also an acute and unmet need for the development of compounds which regulate cell receptor expression per se, as well as an acute need for the identification of compounds which specifically regulate expression of desired target nucleic acids. The present invention satisfies these needs.

SUMMARY OF THE INVENTION

The present invention includes a method of regulating nucleic acid expression in a cell wherein the nucleic acid is selected from the group consisting of a nucleic acid encoding a glycoprotein 180 polypeptide, and a nucleic acid encoding a carboxypeptidase protein. The method comprises contacting a eukaryotic cell with a nucleic acid-expression regulating amount of heparan sulfate, or a biological equivalent thereof, thereby regulating nucleic acid expression in the cell.

In a preferred embodiment, the regulation is inhibition of nucleic acid expression.

In one aspect of the invention, the glycoprotein 180 protein is selected from the group consisting of an avian gp180, and a rodent gp180.

In another aspect of the invention, the carboxypeptidase protein is selected from the group consisting of a bovine carboxypeptidase D, a non-human primate carboxypeptidase D, and a human carboxypeptidase D.

The invention also includes a method of regulating nucleic acid expression in a cell, wherein the nucleic acid encodes a cell receptor protein. The method comprises contacting a eukaryotic cell with a nucleic acid-expression regulating amount of heparan sulfate, or a biological equivalent thereof, thereby regulating nucleic acid expression in the cell.

In a preferred embodiment, the regulation is inhibition of nucleic acid expression.

In one aspect of the invention, the cell receptor protein is selected from the group consisting of a glycoprotein 180, a carboxypeptidase protein, and a carboxypeptidase-like protein.

In another aspect of the invention, the cell receptor protein is selected from the group consisting of an avian gp180, a rodent gp180, a bovine carboxypeptidase D, a non-human primate carboxypeptidase D, and a human carboxypeptidase D.

The invention further includes a method of regulating expression of a cell receptor protein. The method comprises contacting a eukaryotic cell with a nucleic acid-expression regulating amount of heparan sulfate, or a biological equivalent thereof, thereby regulating expression of a cell receptor protein.

In a preferred embodiment, the cell receptor protein is a cell surface receptor protein.

In one aspect, the cell receptor protein is selected from the group consisting of a glycoprotein 180, a carboxypeptidase protein, and a carboxypeptidase-like protein.

In another aspect, the cell receptor protein is selected from the group consisting of an avian gp180, a rodent gp180, a bovine carboxypeptidase D, a non-human primate carboxypeptidase D, and a human carboxypeptidase D.

The invention includes a method of reducing the level of carboxypeptidase activity in a cell. The method comprising contacting a cell comprising carboxypeptidase activity with a nucleic acid-expression inhibiting amount of heparan sulfate, or a biological equivalent thereof, wherein the heparan sulfate, or said biological equivalent thereof, reduces the level of expression of carboxypeptidase in the cell, thereby reducing the level of carboxypeptidase activity in the cell.

In addition, the invention includes a method of identifying a compound capable of regulating expression of gp180. The method comprises contacting a cell capable of expressing gp180 with a test compound, and assessing the level of expression of gp180 in the cell so contacted, wherein a higher or a lower level of expression of gp180 in the cell, compared with the level of gp180 in an otherwise identical cell not contacted with the test compound, is an indication that the test compound is capable of regulating expression of gp180.

In a preferred embodiment, the regulating expression of gp180 is decreased expression of gp180.

In one aspect of the invention, the expression of gp180 is selected from the group consisting of expression of gp180 mRNA and expression of gp180 protein.

In another aspect of the invention, the gp180 is selected from the group consisting of avian gp180, a rodent gp180, a bovine carboxypeptidase D, a non-human primate carboxypeptidase D, and a human carboxypeptidase D.

In yet another aspect of the invention, the cell is selected from the group consisting of a fibroblast, a smooth muscle cell, and an endothelial cell.

The invention also includes a method of treating a human infected with hepatitis B virus. The method comprises administering to the human an antiviral effective amount of heparan sulfate, or a biological equivalent thereof, thereby treating the human infected with hepatitis B virus.

The invention includes a method of inhibiting hepatitis B virus infection in a mammal. The method comprises administering to the mammal a nucleic acid expression regulating amount of heparan sulfate, or a biological equivalent thereof, thereby inhibiting hepatitis B virus infection in the mammal.

Further, the invention includes a method of inhibiting hepatitis B virus infection in a mammal. The method comprises administering an antiviral effective amount of heparan sulfate, or a biological equivalent thereof, to the mammal, thereby inhibiting hepatitis B virus infection in the mammal.

The invention also includes a method of inhibiting hepatitis B virus infection of a cell. The method comprises contacting a cell susceptible to hepatitis B virus infection with an antiviral effective amount of heparan sulfate, thereby inhibiting hepatitis B virus infection.

The invention includes a method of inhibiting hepatitis B virus infection of a cell. The method comprises contacting the cell with a nucleic acid expression regulating amount of heparan sulfate, or a biological equivalent thereof, thereby inhibiting hepatitis B virus infection of the cell.

The invention further includes a method of rendering a cell refractory to hepatitis B virus infection. The method comprises contacting said cell with an antiviral effective amount of heparan sulfate, or a biological equivalent thereof, thereby rendering the cell refractory to hepatitis B virus infection.

The invention also includes a pharmaceutical composition comprising an antiviral effective amount of heparan sulfate, or a biological equivalent thereof.

The invention includes a kit for regulating nucleic acid expression in a cell. The kit comprising a nucleic acid expression-regulating amount of heparan sulfate, or a biological equivalent thereof, and an instructional material for the use thereof.

Additionally, the invention includes a kit for regulating the proliferation of a cell. The kit comprises a nucleic acid expression regulating amount of heparan sulfate, or a biological equivalent thereof, and an instructional material for the use thereof.

The invention further includes a kit for regulating expression of a cell receptor. The kit comprises a nucleic acid expression regulating amount of heparan sulfate, or a biological equivalent thereof, and an instructional material for the use thereof.

The invention includes a kit regulating the level of carboxypeptidase activity in a cell. The kit comprises a nucleic acid expression regulating amount of heparan sulfate, or a biological equivalent thereof, and an instructional material for the use thereof.

The invention also includes a kit for inhibiting hepatitis B virus infection in a mammal. The kit comprises an anti-viral effective amount of heparan sulfate, or a biological equivalent thereof, an applicator, and an instructional material for the use thereof.

The invention further includes a kit for rendering a cell refractory to hepatitis B virus infection. The kit comprises an antiviral effective amount of heparan sulfate, or a biological equivalent thereof, an applicator, and an instructional material for the use thereof.

DETAILED DESCRIPTION OF THE INVENTION

The invention is based on the discovery that the addition of heparan sulfate (HS), or its analog heparin, to pigeon aorta-derived smooth muscle cells (SMCs) inhibits expression of pigeon gp180, a homolog of duck gp180 and human CPD, as evidenced by decreased levels of mRNA encoding gp180 in cells contacted with heparan sulfate.

Thus, the invention encompasses the use of heparan sulfate, heparin, and any biological equivalent thereof, i.e., a compound, for the regulation of expression of cell surface receptors, including, but not limited to, human CPD and gp180.

Further, the invention includes the use of a compound such as heparan sulfate, heparin, and any biological equivalent thereof, for the inhibition of hepatitis B virus infection of cells, because downregulation of gp180 expression by heparan sulfate inhibits infection of cells by hepatitis B virus since gp180 is a cellular receptor protein for the virus. Moreover, the invention includes a method of rendering cells refractory to infection by hepatitis B virus such that cell-to-cell spread of the virus and/or re-infection by the virus is inhibited.

By the general term "gp180," as used herein, is meant avian and rodent glycoprotein 180, and biological equivalents thereof, including bovine and human CPD, a protein sharing between about 60% to about 90% sequence identity with and between about 75% and about 95% sequence similarity with duck gp180 as disclosed herein.

The invention also includes a method of regulating nucleic acid expression in cells by contacting the cells with a compound, preferably heparan sulfate, or its analog heparin, or a biological equivalent thereof such as 2-O-sulfated heparin, 2-O-desulfated heparin, and the like.

By "nucleic acid expression," as that term is used herein, is meant the synthesis of both the RNA and the protein encoded by the nucleic acid. Thus, the term encompasses both the transcription of the ribonucleic acid and the translation of RNA to produce the protein from the nucleic acid encoding the protein. Therefore, although in one embodiment provided herein heparan sulfate caused decreased levels of mRNA encoding a cell receptor protein to be present in the cell, this should in no way be interpreted to limit the invention to decreased expression of a protein due to decreased levels of mRNA. Rather, the present invention encompasses any mechanism whereby decreased levels of protein encoded by a nucleic acid are present in a cell treated with a compound such as heparan sulfate, or a biological equivalent thereof, compared with the level of expression of the same molecule in a cell which is not treated with the compound. That is, the present invention should also be construed to include a heparan sulfate induced decrease in the stability of mRNA encoding a protein such that less mRNA is present in the cell, decreased transcription of mRNA encoding a protein such that less mRNA is present in the cell, or decreased translation of mRNA encoding a protein such that less protein is present in the cell, or any combination of these.

A protein is "encoded," as the term is used herein, by a nucleic acid where the nucleic acid, either DNA or RNA, comprises the genetic information necessary to synthesize the protein.

The term "biological equivalent" means any compound which is capable of mediating an effect substantially similar to contacting a cell with heparan sulfate. For example, a compound which is a "biological equivalent" of heparan sulfate causes a substantially similar decrease in the level of gp180 mRNA or protein when contacted with a cell compared with the level of gp180 mRNA or protein in the cell prior to being contacted with the compound, or when compared with an otherwise identical cell which is not contacted with the compound. Preferably, the decrease in the level of mRNA encoding gp180 (an mRNA approximately 8.0 kb in size) or in gp180 protein present in a cell ranges from about 20% to about 54% or more, and more preferably, by at least about 39% when compared with the level of gp180 mRNA or gp180 protein in the cell prior to being contacted with the compound, or when compared with an otherwise identical cell which has not been contacted with the compound.

In an embodiment of the invention, the biological equivalent of heparan sulfate includes heparin, 2-O-sulfated heparin, and 2-O-desulfated heparin. However, the invention is not limited solely to these biological equivalents of heparan sulfate; rather, the invention is intended to include other compounds having the same ability to regulate gp180 expression in a cell. Such compounds include, but are not limited to, chemically modified as well as chemically depolymerized heparan sulfate, or heparins such as various oligosaccharides produced by partial nitrous acid treatment, and heparan sulfate proteoglycans such as perlecan, or portions thereof. In addition, desulfated and resulfated heparan sulfates should be included in the invention.

In one embodiment of the invention, the nucleic acid which is regulated by heparan sulfate encodes avian gp180. However, the invention is not limited to regulation of expression of nucleic acid encoding avian gp180. Instead, the invention encompasses the regulation of a nucleic acid selected from the group consisting of a nucleic acid encoding a glycoprotein 180, and a nucleic acid encoding a carboxypeptidase, or any fragments or homologs thereof.

The invention should be construed to include, but not be limited to, nucleic acids corresponding to duck gp180, pigeon gp180, rodent, bovine and human CPD.

A nucleic acid is "differentially expressed," as the term is used herein, when the level of mRNA or protein encoded by the nucleic acid is lower in a cell contacted with a compound, when compared with the level of mRNA or protein present in a cell which is not contacted with the compound.

The invention should also not be construed to be limited to the use of pigeon smooth muscle cells as exemplified herein for the assessment of the effect of the compound of the invention on cell receptor protein expression. Instead, the invention includes any avian or mammalian cell that typically expresses gp180 or a protein having an amino acid sequence that is at least about 60% identical and about 80% similar to the sequence of SEQ ID NO:1 (i.e., the sequence of pigeon gp180 shown in Table 1 herein), such as mammalian and avian hepatocytes, and the like.

The term "nucleic acid-expression regulating amount," as used herein, means an amount of a compound, preferably heparan sulfate, or a biological equivalent thereof, which when a cell is contacted with the compound, the level of cell receptor protein in the cell is reduced when compared with the level of cell receptor protein in the cell prior to being contacted with the compound, or when compared with an otherwise identical cell which is not so contacted.

In one embodiment, the nucleic acid-expression regulating amount of heparan sulfate ranges from about 0.1 $\mu$g/ml to about 1000 $\mu$g/ml, wherein maximal inhibition of the level of pigeon gp180 mRNA present in the cell occurs at about 500 $\mu$g/ml of heparan sulfate. However, the invention should not be construed to be limited to these amounts of heparan sulfate. Rather, other ranges of heparan sulfate, heparin, or biological equivalent thereof, may be used and may be easily deduced by the skilled artisan once armed with the present invention.

The nucleic acid-expression regulating amount of a compound is deduced by assessing the level of cell receptor protein (i.e., gp180) mRNA in a cell using an RNA detection assay such as Northern blot analysis, and the like. Further, the level of cell receptor gp180 protein present in a cell can be determined using protein detection assays such as antibody-based assays, and the like. The manner in which nucleic acid expression in a cell is measured is not crucial to the invention and can include nuclear run on, in vitro translation, in situ hybridization, and the like.

In yet another aspect, the invention includes a method of regulating expression of a cell receptor protein by contacting a cell with a compound such as heparan sulfate. Expression of a cell receptor protein is regulated by contacting a cell with the compound in that the compound induces a decrease in the level of expression of the cell receptor protein thus decreasing the level of protein present in the cell. Thus, expression of a cell receptor protein is "regulated" if the level of expression of the protein is higher or lower than the level of expression of the same protein in the cell prior to being contacted with the compound, or compared with the level of expression of the protein in an otherwise identical cell which is not contacted with the compound.

By the term "cell receptor protein," as used herein, is meant a cell protein which, when bound to its ligand, mediates the transmission of a signal to another component of the cell or which causes an effect within the cell when compared with the transmission of the same signal or the same effect in a cell prior to binding of the cell receptor protein to its ligand, or when compared with the transmission of the same signal or the same effect in an otherwise identical cell where the receptor is not bound to its ligand.

In one embodiment, the cell receptor protein gp180, preferably human CPD, and the ligand is heparan sulfate. However, the invention is not limited solely to these cell receptor proteins and this ligand; rather, the invention encompasses other cell receptors, including, but not limited to, other non-human CPDs, and the like, and other ligands including, but not limited to, heparin and other biological equivalents of heparan sulfate, as well as hepatitis B virus, and heparin binding proteins on or associated with the cell surface.

Further, although in one embodiment exemplified herein, the cell receptor protein is located on the surface of a cell, the invention should not be construed to be limited to a cell receptor protein located on the cell plasma membrane. Instead, the cell receptor may be located on both internal and plasma membranes of the cells as is the case for mammalian CPD, and/or the receptor may also be non-membrane-bound and/or located in the cytoplasm of the cell, in secretory vesicles within cells, in lysosomal organelles, in a granular component within cells, and the like.

The invention also includes a method of reducing the level of carboxypeptidase activity in a cell. The method comprises contacting a cell comprising carboxypeptidase activity with a compound such as heparan sulfate, heparin, or a biological equivalent thereof. The level of carboxypeptidase activity in a cell is reduced because the compound induces a reduction in the level of expression of carboxypeptidase mRNA or protein thereby reducing the level of carboxypeptidase activity in a cell.

The term "carboxypeptidase activity," as used herein, means any function associated with or mediated by a carboxypeptidase. Such activity includes, but is not limited to, binding to carboxypeptidase ligands such as human and other hepatitis B viruses, and the like, and/or releasing carboxy-terminal basic amino acid residues from a protein or peptide substrate, and the like.

In addition, the invention includes a method of identifying a compound capable of regulating expression of gp180. The method comprises contacting a cell capable of expressing gp180 with a test compound, and assessing the level of expression of the gp180 in the cell so contacted, wherein a higher or a lower level of expression of the gp180 in the cell, compared with the level of gp180 in an otherwise identical cell not contacted with the test compound, is an indication that the test compound is capable of regulating expression of gp180. The expression of gp180 which is assessed may be expression of gp180 mRNA and/or expression of gp180 protein. Further, the gp180 expression being measured may be any of avian gp180, a rodent CPD, a bovine CPD, and a human CPD. In addition, the type of cells to be used in the assay may be of mesenchymal origin such as fibroblasts, smooth muscle cells, such cells being either transformed or nontransformed. Additionally, the cells used in the assay include endodermally-derived cells such as, but not limited to, endothelial cells, wherein the cells may be either transformed or nontransformed.

One skilled in the art would appreciate based upon the disclosure provided herein that nucleic acids whose expression is regulated by a compound such as heparan sulfate, or a biological equivalent thereof, may be identified by differential RNA display assay. However, the invention should not be construed to be limited to this, or any other, particular method of measuring a change in the level of nucleic acid expression. Rather, as set forth elsewhere herein, the invention includes other methods of detecting a change in the level of nucleic acid expression.

In one embodiment exemplified herein, the nucleic acid whose expression is regulated is nucleic acid encoding pigeon gp180. Further, regulation of expression is demonstrated by decreased level of gp180 mRNA in cells using differential RNA display assays. Thus, inhibition of nucleic acid expression by heparan sulfate may be demonstrated by decreased mRNA levels in a cell. However, the present invention is not limited to detecting inhibition of nucleic acid expression by decreased mRNA levels or to using differential RNA display assay. Rather, as discussed previously elsewhere herein, the invention encompasses other methods for detecting inhibition of nucleic acid expression including, but not limited to, demonstrating decreased level of a protein in a cell contacted with heparan sulfate, compared with the level of the protein in a cell before contact with heparan sulfate, or compared with an otherwise identical cell not contacted with heparan sulfate.

The invention also includes a method of treating a human infected with hepatitis B virus. The method comprises administering an antiviral effective amount of a compound such as heparan sulfate, heparin, or a biological equivalent thereof, to a human infected with hepatitis B virus thereby treating the human. Treatment of the human with the compound results in a decrease in the level in a cell of the receptor for hepatitis B virus. Thus, the virus is unable to infect cells and replicate therein. Virus which cannot replicate should then be cleared by the immune system. In this manner, administration of the compound to a human infected with hepatitis B virus serves to treat and/or alleviate the infection.

The term "hepatitis B virus infection," as used herein, is intended to encompass acute hepatitis B virus infection, chronic hepatitis B virus infection, acute and chronic hepatitis B virus infection, and hepatitis B virus-induced and/or associated hepatocellular carcinoma.

The term "treating," as it is used herein, refers to reducing the frequency with which a symptom of the hepatitis B virus infection is experienced, or to a lessening of the severity of the symptoms experienced by a human infected with the virus compared with the human prior to treatment.

By the term "alleviating," as the term is used herein to refer to a disease, is meant reducing the severity of the symptom(s) associated with the subject disease.

In another aspect, the invention includes a method of inhibiting hepatitis B virus infection in a mammal. The method comprises administering a nucleic acid expression regulating amount of a compound such as heparan sulfate, or a biological equivalent thereof, to a mammal thereby inhibiting hepatitis B virus in a mammal. Administration of the compound inhibits hepatitis B virus in that the compound reduces the level of expression of a cell receptor protein involved in virus entry into a cell. Reduction in the cell receptor protein thereby prevents virus entry into cells thus, in turn, impeding virus replication. Virus which cannot enter cells or replicate is presumably cleared by the immune system. In this manner, administration of the compound inhibits virus infection in a mammal.

By "inhibiting hepatitis B virus infection," as used herein, is meant preventing infection of cells by a virus, preventing replication of a virus in cells, or reversing a physiological effect of virus infection on the cells. The terms "nucleic acid expression regulating amount" and "biological equivalent" are defined elsewhere herein.

It will be appreciated by one skilled in the art based upon the disclosure provided herein that the method of the invention encompasses inhibiting hepatitis B virus infection by decreasing the level of expression of its receptor, i.e., gp180 or CPD, in a cell otherwise susceptible to hepatitis B virus infection where virus infection is mediated at least in part by hepatitis B virus binding to the receptor.

In yet another aspect, the invention includes a method of inhibiting 1 hepatitis B virus infection in a mammal. The method comprises administering an antiviral effective amount of a compound such as heparan sulfate, or a biological equivalent thereof, to a mammal. The compound reduces the expression of a cell receptor protein available for virus binding to cells, thereby inhibiting virus adsorption and entry into the cells. Virus which cannot enter cells is incapable of replicating therein and is cleared by the immune system thereby inhibiting hepatitis B virus in the mammal.

One skilled in the art would appreciate based on the disclosure herein that the antiviral activity of heparan sulfate with regard to hepatitis B virus is mediated by a decreased level of expression of a cell receptor for the virus caused by heparan sulfate. Thus, the novel antiviral effect of heparan sulfate, or a biological equivalent thereof, as disclosed herein is mediated by a decrease in the cell receptor protein available to bind the virus which, in turn, mediates a decrease in the ability of the virus to enter and thereby infect the cell.

Also, the invention includes a method of inhibiting hepatitis B virus infection of a cell. The method comprises contacting a cell susceptible to hepatitis B virus infection with an antiviral effective amount of a compound such as heparan sulfate, or a biological equivalent thereof, thereby inhibiting hepatitis B virus infection. As disclosed previously elsewhere herein, the compound reduces the expression of a cell receptor protein involved in virus adsorption to and entry into a susceptible cell. Accordingly, the compound inhibits virus binding to the receptor and blocks subsequent virus entry into the cell where the virus would otherwise replicate. In this manner, the compound inhibits virus infection by reducing the availability of the virus receptor which otherwise mediates virus entry into cells.

One skilled in the art would appreciate based on the disclosure provided herein that an antiviral effective amount exerts its effect by reducing the level of expression of a cell receptor for hepatitis B virus including, but not limited to, gp180, a carboxypeptidase protein, and a carboxypeptidase-like protein. However, the level of inhibition of infection need not be directly correlated'to the level of reduction of gp180 or CPD expression detected.

By "carboxypeptidase-like protein," as the term is used herein, is meant a protein with minor domains possessing homology to the carboxypeptidases such as, for example, the aortic CP-like protein (ACLP) described by Layne et al. (1998, J. Biol. Chem. 273:15654–15660), and the like.

The invention further includes a method of inhibiting hepatitis B virus infection of a cell. The method comprises contacting a cell with a nucleic acid expression regulating amount of heparan sulfate, or a biological equivalent thereof, thereby inhibiting hepatitis B virus of the cell. One skilled in the art would appreciate based on the disclosure herein that the compound inhibits virus infection by decreasing the level of expression of a cell receptor protein thereby reducing the amount of cell receptor protein available to the virus. Virus which is unable to enter the cell and replicate is presumably cleared by the immune system. Thus, the compound inhibits hepatitis B virus infection of a cell by decreasing the amount of cell receptor protein present to mediate virus entry into the cell.

The invention also includes a method of rendering a cell refractory to hepatitis B virus infection. The method comprises contacting a cell with an antiviral effective amount of a compound such as heparan sulfate, or a biological equivalent thereof, thereby rendering the cell refractory to hepatitis B virus infection. The compound renders the cell refractory by reducing the level of expression of cell receptor mRNA and protein in the cell. This reduced expression, in turn, decreases the amount of cell receptor protein available for virus binding and entry into the cell. The virus, which is unable to enter the cell, is cleared by the immune system thus rendering the cell refractory to virus infection.

By the term "refractory to infection," as the term is used herein, is meant that the cell is able to resist infection by hepatitis B virus in that it is not infected by the virus or, if infected, does not exhibit any effect(s) otherwise associated with virus infection, and/or the cell does not produce any infectious or non-infectious virus particles.

The invention also includes a pharmaceutical composition comprising an antiviral effective amount of heparan sulfate, or a biological equivalent thereof. The composition comprises a pharmaceutically acceptable carrier.

Typically, dosages of the compound of the invention which may be administered to an animal, preferably a human, range in amount from 1 $\mu$g to about 100 mg per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 1 mg to about 100 mg per kilogram of body weight of the animal.

One skilled in the art would appreciate based on the disclosure herein that the invention includes administration of a dose which results in a concentration of uronic acid, as a measure of the amount of heparan sulfate present therein, between about 0.1 $\mu$g/ml to about 1000 $\mu$g/ml in the tissue of a hepatitis B virus infected human or of a blood tissue of the human.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the veterinary or human patient being treated, and the like.

As used herein, the term "antiviral effective amount" means an amount of a compound, which when delivered to or administered to a human infected with hepatitis B virus, is capable of preventing replication of a virus in the cell, preventing infection of the cell by hepatitis B virus, or reversing a physiological effect of infection of the cell by a virus. Antiviral compounds and antiviral effective amounts thereof are well known and described in the literature. By way of example, AZT (zidovudine, Retrovir® Glaxo Wellcome Inc., Research Triangle Park, N.C.) is an antiviral agent which is thought to prevent replication of HIV in human cells.

By the term "administering," as the term is used herein, is meant any means or method of providing the antiviral effective amount of heparan sulfate, or a biological equivalent thereof, to a human.

One skilled in the art would appreciate based on the disclosure herein that the compound, such as heparan sulfate, or a biological equivalent thereof, would be administered to a human in a pharmaceutically-acceptable carrier.

As used herein, the term "pharmaceutically-acceptable carrier" means a chemical composition with which heparan sulfate, or a biological equivalent thereof, may be combined and which, following the combination, can be used to administer a compound to a mammal, preferably a human, in need of the compound.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the compound such as heparan sulfate, or a biological equivalent thereof, according to the methods of the invention.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium laurel sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro (ed., 1985, Remington's Pharmaceutical Sciences, Mack Publishing Co., Easton, Pa.), which is incorporated herein by reference.

The invention includes various kits which comprise a compound, such as heparan sulfate, or a biological equivalent thereof, pharmaceutical compositions, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for regulating nucleic acid expression in a cell. The kit is used pursuant to the methods disclosed in the invention. Briefly, the kit may be used to contact a cell with a nucleic acid expression regulating amount of heparan sulfate, or a biological equivalent thereof, as these terms have been previously defined elsewhere herein. Moreover, the kit comprises a nucleic acid expression regulating amount of heparan sulfate, or a biological equivalent thereof, in a pharmaceutically-acceptable carrier, and an instructional material for the use of the kit. These instructions simply embody the examples provided herein.

The kit includes a pharmaceutical composition comprising a compound such as heparan sulfate, or a biological equivalent thereof, in a pharmaceutically-acceptable carrier. The composition is provided in an appropriate antiviral effective and/or nucleic acid expression regulating dose as set forth elsewhere herein. Further, the route of administration and the frequency of administration are as previously set forth elsewhere herein.

The invention further includes a kit for regulating the proliferation of a cell. The kit comprises a nucleic acid expression regulating amount of heparan sulfate, or a biological equivalent thereof, and an instructional material for the use of the kit. The instructions simply embody the examples provided herein. Further, the terms "nucleic acid expression regulating amount" and "biological equivalent" have been previously defined elsewhere herein.

The invention also includes a kit for regulating expression of a cell receptor. The kit comprises a nucleic acid expression regulating amount of heparan sulfate, or a biological equivalent thereof, and an instructional material for the use of the kit. The instructions simply embody the examples provided herein.

The invention also includes a kit for regulating the level of carboxypeptidase activity in a cell. The kit comprises a nucleic acid expression regulating amount of heparan sulfate, or a biological equivalent thereof, and an instructional material for the use of the kit, which instructional material simply embodies the examples provided herein.

In addition, the invention includes a kit for inhibiting hepatitis B virus infection in a mammal. The kit comprises an anti-viral effective amount of heparan sulfate, or a biological equivalent thereof, an applicator, and an instructional material for the use of the kit. The instructions for using the kit depend on the particular mammal for which the kit is to be used and the method of delivery of the heparan sulfate, or a biological equivalent thereof.

By the term "applicator" as the term is used herein, is meant any device including, but not limited to, a hypodermic syringe, a pipette, and the like, for administering the heparan sulfate, or biological equivalent thereof, to a mammal.

The kit may also include instructions on how to administer the compound such as heparan sulfate, or a biological equivalent thereof, using the applicator provided therewith.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Heparan Sulfate Regulates Expression of Nucleic acid Encoding Carboxypeptidase/gp180 in Smooth Muscle Cells The experiments presented in this example may be summarized as follows.

Heparan sulfate, a constituent of cell surface syndecans, functions as an endogenous regulator to inhibit cell growth in many cells as reviewed by Carey (1997, J. Biochem. 327:1–16). In order to determine which, if any, genes in cultured pigeon artery smooth muscle cells are selectively influenced by exogenous HS, a differential RNA display technique described by McClelland et al. (1993, In: The State of the Science, at 103–115, Pena et al., eds., Birkhauser-Verlag, Switzerland) was used as modified by Clontech Laboratories, Inc. (Delta Differential Display Kit, Cat. No. K1810-1, Palo Alto, Calif.) following the manufacturer's instructions. Thirty cDNA bands reproducibly regulated by HS were identified by comparison to non-HS-treated cells. One cDNA fragment of about 500 base pairs in length exhibited a high sequence identity (i.e., 91% identity) to duck gp180, a member of the carboxypeptidase family of proteins. Moreover, the 500 bp pigeon cDNA clone exhibited 92% sequence identity to human CPD. Carboxypeptidase D has only recently been identified and its function(s) has not yet been elucidated (Song and Fricker, 1996, J. Biol. Chem. 271:28884–28889; Xin et al., 1997, DNA and Cell. Biol. 16:897–909). Further, the DNA encoding duck gp180 was sequenced and the protein has been identified as a homolog of mammalian carboxypeptidase D and as a cell receptor for hepatitis B virus (Kuroki et al., 1995, J. Biol. Chem. 270:15022–15028; McGwire et al., 1997, Life Sci. 60:715–724).

Pigeon smooth muscle cells provide an advantageous system in which to study heparan sulfate regulation of gene expression. This is due to the availability of SMC lines of White Carneau (WC) atherosclerosis-susceptible pigeons exhibiting enhanced growth compared with the SMCs of Show Racer (SR) pigeons as demonstrated by Bortoff and Wagner (1995, Mol. Biol. Cell. 6:13. Without wishing to be bound by theory, gp180 may participate in a mechanism linked to enhanced cell growth and, perhaps, to susceptibility to atherosclerosis. The data disclosed herein demonstrate that SMCs treated with HS exhibit reduced gp180 gene expression. Although there may be other mechanisms for downregulating gp180 gene expression as demonstrated by the reduced gp180 expression in serum-starved growth-inhibited SMCs, the data disclosed herein demonstrating the specific downregulation of gp180 expression by HS suggest specific therapeutic approaches using heparin-like molecules.

The Materials and Methods used in the experiments presented in this example are now described.

Cells

Smooth muscle cell cultures were prepared from aortic explants as described in Smith et al. (1979, Exp. Mol.

Pathol. 30:190–208). Briefly, thoracic aortas just proximal to the left and right subclavian arteries and including the innominate artery to 0.5 cm distal to the celiac bifurcation, were removed from 3-day-old pigeon squabs. The aortic tissue was cleaned of connective tissue and blood and opened longitudinally. The adventitia and outer one-third of the media were removed and discarded. The arterial intima and luminal portions of the medial tissue were minced with a scalpel and were digested with 0.5 mg/ml collagenase A (Sigma Chemical Co., St. Louis, Mo.) in Dulbecco's Modified Eagle's Medium/F12 medium containing 100 U/ml penicillin and 100 µl/ml streptomycin sulfate ("explant media"). The tissue was centrifuged and the tissue pellet was washed once with explant media. The pellet was resuspended in Dulbecco's Minimum Essential Media/F12 with Earle's Base Salts supplemented with 100 U/ml penicillin, 100 µl/ml streptomycin sulfate, 200 mM/l L-Glutamine, Eagle's Minimal Essential Medium vitamins, and 10% fetal bovine serum (complete media) and the cells were plated in 35 mm dishes in complete media.

Differential RNA Display Assay

A modified differential RNA display assay was performed using a Clontech Delta™ Differential Display Kit (Cat. No. K1810-1, Clontech Labs., Inc., Palo Alto, Calif.) per the manufacturer's instructions.

Total RNA was isolated from WC pigeon aorta-derived SMCs in logarithmic growth and from otherwise identical SMCs treated for 24 hours with 20 µg/ml of bovine kidney heparan sulfate (Cat. No. 64007001, Seikagaku America, Inc., Ijamsville, Md.). Modified display reactions were performed using a Clontech Delta™ RNA Fingerprinting kit (Clontech Laboratories, Inc., Palo Alto, Calif.) per the manufacturer's instructions. The resulting amplified cDNA products were separated on a 4.5% bis-acrylamide sequencing gel, and the gel was dried and exposed to autoradiography for 16–24 hours.

Selected cDNAs that demonstrated differential expression between the untreated logarithmic-growth SMCs and the heparan sulfate-treated logarithmic growth SMCs were excised and eluted from the gel. The selected cDNAs were re-amplified using the same primers and conditions used in the original display reaction as provided in the kit per protocol PT 1173-1. Primer P3 (5'ATTAACCCTCACTAAATGCTGGTGG3') (SEQ ID NO:2) and T2 (5'CATTATGCTGAGTGATATCTTTTTTTTTAC3') (SEQ ID NO:3) were used for the 500 bp cDNA fragment PCR amplification product which hybridized to an 8.0 kb mRNA by Northern blot analysis as described below.

The isolated PCR amplification products of the selected cDNAs were random-prime labeled with $^{32}$P-dATP (ICN Biochemicals, Irvine, Calif.) and used as probes for Northern blot analysis. Further, the PCR amplification products were cloned into the pGEM-T vector System II (Promega Corp., Madison, Wis.), per the manufacturer's instructions.

Northern Blot Analysis

Northern blot analysis was performed by standard methods such as those described in, for example, Ausubel et al. (1994, Analysis of RNA by Northern and slot blot hybridization, In: Current Protocols in Molecular Biology, pages 4.91–4.94, Green & Wiley, New York).

The Results of the experiments presented in this example are now described.

Cells Treated with Heparan Sulfate Exhibit Decreased Level of gp180 Expression

Of the isolated PCR amplification products, a cDNA fragment of approximately 500 bp (SEQ ID NO:1) was selected which hybridized to an 8.0 kb mRNA by Northern blot analysis. The cDNA was sequenced and the nucleotide sequence and deduced amino acid sequence (SEQ ID NO:1) were obtained. A BLAST amino acid sequence identity search was performed revealing 92% identity of the 500 bp clone to carboxypeptidase D and to gp180 (Anas sp). The sequence of the cDNA clone was compared to other CPDs and the results of the comparison are presented in Table 1.

TABLE 1

| Pigeon | 1 | MLVEVHKGVHGEVQDKSGKAISKATIVLNESERVYTKEGGYFHVLLAPGE |
| --- | --- | --- |
| Duck CPD | 1214 | MLVEVHKGVHGEVQDKSGKAISKATIVLNEGERVYTKEGGYFHVLLAPGE |
| Rat CPD | 1205 | MLVEVHKGVHGEVKDKTGKPISKAVIVLNEGERVETKEGGYFHVLLAPGV |
| Human CPD | 1204 | MLVEVHKGVHGEVKDKTGKPISKAVIVLNEGEKVQTKEGGYFHVLLAPGV |
| | | |
| Pigeon | 51 | HNINAIADGYQQKHYKVEVRHDAPSSVEIVFDEENRIFGLPRELVVTVAG |
| Duck CPD | 1264 | HNINAIADGYQQKHMKVEVRHDAPSSVEIVFDNENRIFGLPRELVVTVAG |
| Rat CPD | 1255 | HNINAIADGYQQQHSQVEVRHDAASSVVIVFDEENRIFGLPRELVVTVSG |
| Human CPD | 1254 | HNIEAIADGYQQKHSQVEVRHDAASSVVIVFDEENRIFGLPRELVVTVSG |
| | | |
| Pigeon | 101 | ASMSALVLTACIIWCVCSIKSNRHKDGFERLRQHHDEYEDEIRMMST |
| Duck CPD | 1314 | ASMSALVLTACIIWCVCSIKSNRHKDGFERLRQHHDEYEDEIRMMST |
| Rat CPD | 1305 | ATMSALELTACIIWCECSIKSNRHKDGFERLRQHHDEYEDEIRMMST |
| Human CPD | 1304 | ATMSALELTACIIWCECSIKSNRHKDGFERLRQHHDEYEDEIRMMST |

The amino acid differences between pigeon (SEQ ID NO:1) and other CPDs (duck {SEQ ID NO:4}, cat {SEQ ID NO:5} and human {SEQ ID NO:6}) are shaded. The amino acid residues comprising a putative transmembrane region are underlined.

The BLAST amino acid sequence search did not reveal any other proteins which shared high homology with the 500 bp pigeon gp180 cDNA. Human, mouse and rat CPE each only share 8.7% identity with pigeon cDNA, while human aortic CP-like protein (ACLP; Layne et al., 1998, J. Biol. Chem. 273:15654–15660) and human adipocyte lipid binding protein 1 (AEBP1; He et al., 1995, Nature Lett. 378:92–96; Ohno et al., 1996, 1996, Biochim. Biophys. Res. Commun. 228:411–414) share 15.3% and 14.7%, respectively, with pigeon cDNA.

Figure 1:
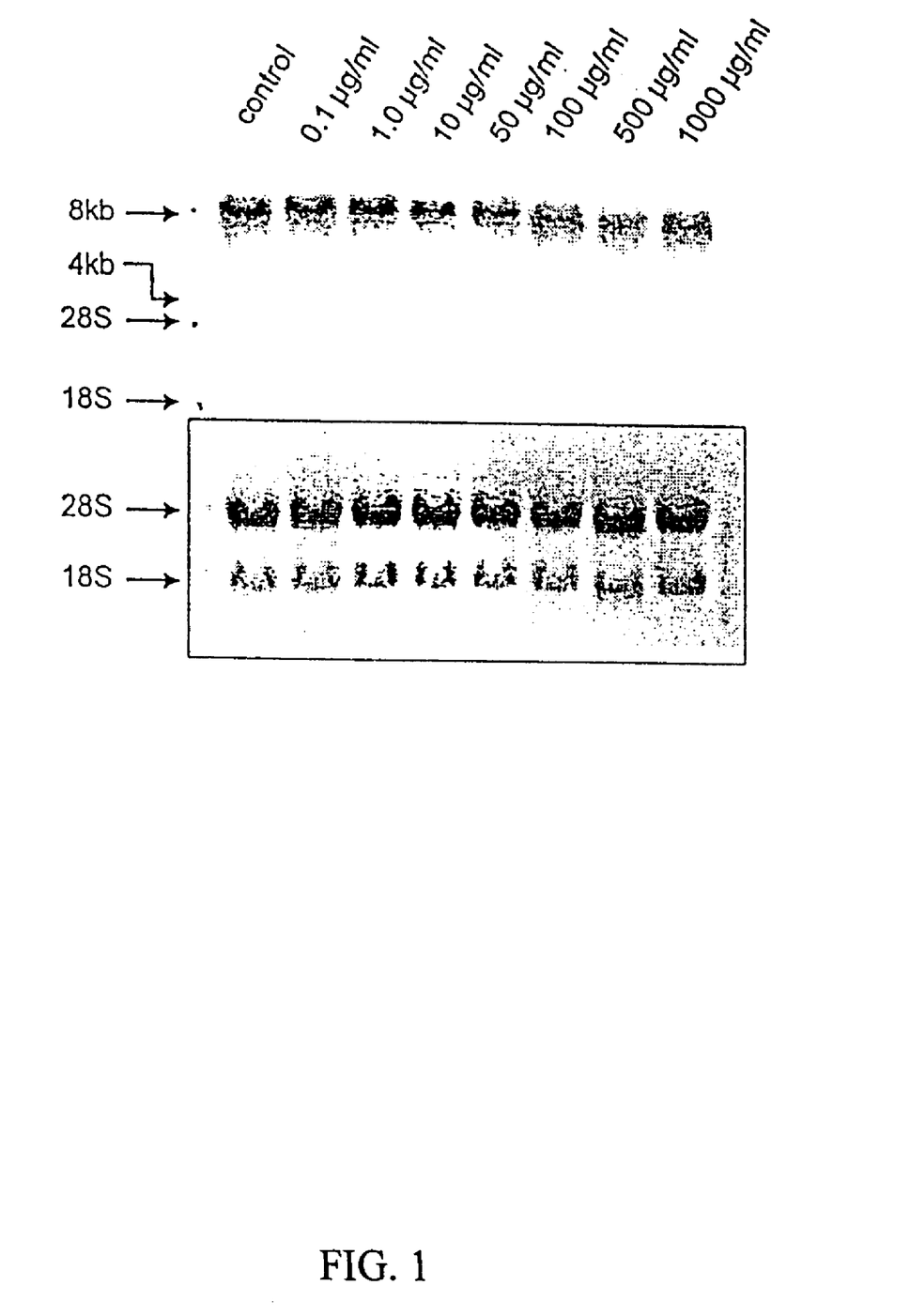
FIG. 1 is an image of a Northern blot depicting the inhibition of gp180 mRNA (i.e., a transcript of about 8 kb) expression by increasing amounts of heparan sulfate.

Following identification of the 500 bp pigeon cDNA fragment, the dose responsive effect of HS on gene expression was examined. Duplicate cultures of WC pigeon artery-derived SMCs in the logarithmic growth phase were treated with 0.1, 1.0, 10, 50, 100, 500, and 1000 µg/ml of HS (as determined by measurement of uronic acid content as described in Blumenkrantz and Asbue-Hansen, 1973, Anal. Biochem. 54:484–489). After 24 hours, total RNA was isolated from each SMC culture, and the RNA was analyzed by Northern blot hybridization. Northern blot analysis demonstrated that increasing concentrations of HS significantly inhibited gp180 gene expression (FIG. 1). Following densitometric scans of the autoradiograms and correcting for minor differences in RNA loaded onto each gel lane, a maximal inhibition of 54% of gp180 gene expression was observed in the presence of 500 µg/ml of HS. It is important to note that the SMCs were not synchronized. Without wishing to be bound by theory, it is expected that the effects of HS on cell proliferation may be more pronounced on synchronized logarithmic growth or confluent cultures of SMCs.

Specific Oligosaccharide Residues of Heparan Sulfate Mediate the Anti-proliferative Gene Regulation Effects Specific oligosaccharide residues of HS that contain disaccharides enriched in 2-O-sulfated glucuronic acid are essential for the anti-proliferative activity of cell surface HS. Therefore, a preparation of heparin lacking sulfate at the C-2 position of hexuronic acid as described in Maccarana et al. (1993, J. Biol. Chem. 268:23898–23905) was used to determine the structural properties of HS necessary for gene regulation. For these studies, total RNA was isolated from identical cultures of WC SMC in logarithmic growth treated for 24 hours with bovine kidney HS containing 2-O-sulfate groups, 2-O-desulfated heparin, or no HS. Treatments with 2-O-sulfated heparin inhibited gp180 gene expression by 39% while treatments with 2-O-desulfated heparin inhibited gp180 expression by 20% as determined by densitometric scans of the autoradiograms as described previously elsewhere herein.

The data disclosed indicate that while specific HS oligosaccharide sequences containing 2-O-sulfated hexuronic acid may be essential for inhibition of SMC proliferation, a sulfate at position C-2 may not be absolutely required for the downregulation effects observed on gp180 gene expression by heparan sulfate. Without wishing to be bound by theory, these data suggest differential effects of HS on cell proliferation and on gp180 gene expression dictated by structural specificity of oligosaccharides of HS.

Gene Expression Levels of gp180

Gene expression is assessed in five separate cell lines each of SMCs derived from WC and SR pigeons. Each line of pigeon SMCs was derived from a separate 1–3 day-old pigeon from a different breeding pair and frozen cell stocks were prepared. In this way, the level of gene expression of gp180 in WC SMCs is compared to the level of expression in SR cells. RNA is isolated from cells at logarithmic growth and at confluence. Without wishing to be bound by theory, a lower level of expression in WC compared with expression level in SR SMCs is expected following Northern blot analysis and, in both cell lines, highest expression is expected at confluence. Correlation of message level to protein level in cells is established as a statistically significant relationship between message level and protein level.

EXAMPLE 2

Cloning and Sequencing Pigeon gp180

The experiments presented in this example may be summarized as follows.

Standard cloning procedures are used to obtain the entire, full-length sequence of pigeon SMC gp180 cDNA.

Cells

Pigeon aortic smooth muscle cells are obtained as described previously elsewhere herein and described in Bortoff and Wagner (1995, Mol. Cell. Biol. 6:13).

Lambda gt-10 Library Screening

The pigeon aorta λgt-10 library is the kind gift of Dr. Charles Boyd (University of Medicine and Dentistry of New Jersey, NJ).

RACE Cloning System

The Rapid Amplification of cDNA Ends (RACE) cloning system is purchased from Gibco-BRL Life Technologies (Cat. No. 18374-058, Rockville, Md.) and used per the manufacturer's instructions.

Cloning and Screening of Full-length Pigeon gp180 cDNA

In order to obtain full-length pigeon gp180 cDNA clones, an embryonic WC pigeon aorta λgt-10 cDNA library obtained from Dr. Charles Boyd is screened as follows. The optimal phage titer is determined and recombinant phage are incubated with C-600 *E. coli* plating bacteria. The bacteria are plated on LB plates and a nylon filter is placed on the plates containing phage plaques. The nylon membranes are processed using a Microwave Screening Kit (Invitrogen, Carlsbad, Calif.) per the manufacturer's instructions. The nylon membranes are probed with a $^{32}$P-labeled gp180 riboprobe and the positive plaques are selected and placed in the wells of a 96-well plate containing LB broth and plating bacteria. An aliquot of the lysed bacterial suspension from each well of the 96-well plate is applied to a 96-well dot blot apparatus (Bio-Rad Laboratories, Richmond, Calif.) containing a pre-wetted filter. After fluid aspiration, the nylon membrane is removed from the dot blot apparatus and baked. The nylon membrane is then used in subsequent screening rounds until the entire pigeon gp180 cDNA sequence is obtained.

Alternatively, full-length clones are obtained using a 5' RACE System kit (Life Technologies, Inc., Gaithersburg, Md.). Using nested oligonucleotide primers closest to the 5' end (or the 3' end if necessary) of the gp180 sequences obtained, the first cDNA strand is synthesized. An anchor sequence using Tdt and dCTP is added to the 3' end of the cDNA along with nested 5' gp180 primers (which include a restriction endonuclease site at the 5' end) and PCR amplification is performed per the manufacturer's instructions. Further rounds of PCR amplifications may be performed to obtain a more homogeneous product.

The resulting RACE products are gel-purified using the Wizard PCR prep purification system (Promega Corp., Madison, Wis.). The resulting purified products are sequenced by standard sequencing methods as described in, for example, Sambrook et al. (1989, Molecular Cloning: A Laboratory Manual, Cold Spring Harbor Laboratory, New York), and Ausubel et al. (1997, Current Protocols in Molecular Biology, Green & Wiley, New York).

The pigeon gp180 cDNAs obtained are subcloned into PMHTM (Boehringer Mannheim, Indianapolis, Ind.), a eukaryotic expression vector containing a carboxy-terminal epitope tag, according to the manufacturer's instructions.

Riboprobe Synthesis and Southern Blot Analysis cDNAs obtained as previously described herein containing gp180 sequences are unidirectionally subcloned into the pMH™ vector and then they are sequenced allowing confirmation of proper insert orientation. The clones are linearized by restriction endonuclease digestion and purified. The SP6 promoter is used to synthesize an antisense mRNA, using the riboprobe In Vitro Transcription System (Promega Corp., Madison, Wis.). Briefly, one mg/ml of the cDNA template is incubated with RNasin, NTPs, $^{32}$P-UTP, and SP6 RNA polymerase. The riboprobe is used to detect plaques in the λgt-10 library which contain gp180 sequences.

For Southern blot analysis, the nylon membranes are incubated at 65° C. in a prehybridization solution (2× Denhardt's, 1% SDS, 0.5% non-fat dry milk, 0.00% thimerosal and 100 mg/ml denatured yeast tRNA). Following pre-hybridization, target gp180 sequences from the λgt-10 library are identified by hybridization at 65° C. overnight with $^{32}$P-labeled gp180. The membranes are washed stringently in 2×SSC and 0.1% SDS, and then in 0.1×SSC and 0.1% SDS, dried, and exposed to X-ray film. Following cloning, alignment sequence maps are prepared to compare rat CPD, human CPD, and duck gp180 to pigeon gp180 to determine sequence similarities.

Characterization of Pigeon gp180

To confirm that the gp180 cDNA is properly translated and processed, COS cells are transiently transfected with pigeon gp180 cDNAs using the DEAE-dextran transfection method as described in, for example, Sambrook et al (1989, Molecular Cloning: A Laboratory Manual, Cold Spring Harbor Laboratory Press, Cold Spring Harbor, N.Y.). Briefly, COS cells, which may be obtained from American Type Culture Collection (ATCC Accession No. CRL-1650, American Type Culture Collection, Rockville, Md.), are plated into 100 mm plates to achieve approximately 60–75% confluency within 24–30 hours. For transfection of COS cells, about 6 micrograms of full-length gp180 cDNA subcloned into the multiple cloning site of the mammalian expression vector pMH™ are used per each 100 mm culture plate. This expression vector utilizes the SP6 and T7 enhancer/promoter regulatory region, SV40 polyadenylation signal, and contains a carboxy-terminal hemagglutinin (HA) epitope tag allowing detection and recovery of transfectants using anti-HA antibodies. Cells are washed with tris-buffered saline (TBS) and the cDNA-DEAE-dextran mixture (5 mg/ml) in Dulbecco's Modified Eagle's Medium (DMEM) containing 10% fetal bovine serum (FBS) and 100 mm chloroquine is added to the COS cells. Following incubation at 37° C., the cells are washed with TBS and DMEM containing 10% glycerol is added to the cells. Following a four minute incubation, the DMEM/glycerol media is removed from the cells, the cells are washed with TBS, and DMEM is added to the cells which are then incubated at 37° C. for about 48–60 hours. The cells are also plated on glass chamber slides and are used for immunohistochemistry staining. Also, transfected COS cell lysates are prepared for large-scale purification of gp180.

Immunodetection of Pigeon gp180 in Transfected COS Cells

The anti-HA mouse monoclonal antibody, specific for the HA epitope tag, is used to determine the relative efficiency of transfection. Following transfection, the cells are fixed in 3.5% paraformaldehyde containing 0.1% Tween-20. The cells are washed with phosphate buffered saline (PBS) and non-specific antibody binding sites are blocked. Anti-HA antibody (at a concentration ranging from about 1 to about 10 mg/ml) is added to the slide and the slide is incubated for 30 minutes. The cells are rinsed and incubated first with an unconjugated anti-HA epitope tag (primary) antibody then with a peroxide conjugated (secondary) antibody recognizing the anti-HA epitope tag antibody (Boehringer Mannheim Corp., Indianapolis, Ind.). Additionally, the cell nuclei are stained with hematoxylin as described in Lynch et al. (1969, In: Medical Laboratory Technology, W.B. Saunders Co., Philadelphia, Pa.), and the cells are examined visually to assess immunodetectable HA epitope tag and to determine transfection efficiency.

Purification of Pigeon gp180

Pigeon gp180 from transfected COS cells is purified by affinity chromatography as follows. Briefly, approximately 2 mg of mouse monoclonal anti-HA antibodies are coupled to 1 ml protein A agarose (Boehringer Mannheim Corp., Indianapolis, Ind.) and the beads are incubated at room temperature with gentle rocking to bind the anti-HA antibodies to the beads. The beads are washed with 0.2 M sodium borate, then the beads are centrifuged, and resuspended in 10 volumes of 0.2 M sodium borate containing 20 mm dimethylpimelimidate, and washed with 0.2 M ethanolamine (pH 8.0). Following centrifugation, the beads are resuspended in PBS containing 0.01% merthiolate and poured as a column.

Transfected COS cells containing gp180 protein are lysed in 1 ml PBS containing 1% NP-40 extraction buffer also containing 1 mm EGTA, 0.1 ng/ml aprotinin, 0.2 mg/ml AEBSF [4-(2-aminoethyl)-benzenesulfonyl fluoride, HCl], 10 μg/ml pepstatin, for 20 minutes on ice. The plates are scraped and the lysate is centrifuged at 10,000×g for 30 minutes at 4° C. An aliquot of the supernatant is analyzed using bicinchonic acid (BCA) to determine the protein concentration per a Micro BCA Protein Assay (Pierce Chem. Co., Rockford, Ill.) per manufacturer's instructions. The remaining supernatant is diluted 10-fold in 8M urea and applied to the protein A-anti-HA affinity column. The affinity column is washed to remove contaminating cell protein until the adsorption ($A_{280}$) is below 0.01 and then the recombinant gp180 recombinant protein is eluted with 8 M urea.

Carboxypeptidase Studies

Pigeon gp180 isolated from transfected COS cells, as well as from membranes of SMCs, is used as the starting material for carboxypeptidase studies. The studies indicate whether the expressed protein, as well as membrane preparations, contain enzymatic activity consistent with that described for CPD.

Carboxypeptidase activity is measured using a fluorogenic assay using a dansyl-phe-ala-arg substrate in 0.1 M NaAc, pH 5.5, containing 0.1% Triton X-100 (Fricker, 1995, Methods Neurosci. 23:237–250). For inhibition of the enzymes, samples are pre-incubated with inhibitors for 10 minutes. Experiments demonstrating specific requirements for the release of CP activity from SMC membrane fractions are performed as described in Fricker et al. (1990, J. Biol. Chem. 265:2476–2482). The membrane fractions are pelleted at 100,000×g and are resuspended in 0.1 M NaAc buffer containing Triton X-100. Aliquots are added to equal volumes of appropriate buffers, at specific salt or pH levels, the samples are then incubated at 4° C. for two hours with constant mixing and then centrifuged at 100,000×g for one hour. The resultant supernatants and pellets are assayed for carboxypeptidase activity.

Biochemical Characterization of Pigeon gp180 Carboxypeptidase Activity

Experiments are performed to identify recombinant pigeon gp180 and on SMCs as CPD and to distinguish the enzyme from other CPs. First, the conditions described for CPD (Song and Fricker, 1995, J. Biol. Chem. 270:25007–25013) are used to demonstrate activity of the recombinant and/or SMC-associated pigeon gp180. Isolated placental CPE is a positive control in the CP assay. The pH optimum is 5.5, which is the optimum pH for CPD and CPE activity, rather than pH 7.5 (optimum for CPM). CPE exhibits pH and salt-dependent release from membranes (Fricker et al., 1990, J. Biol. Chem. 265:2476–2482). Therefore, membranes from cells are treated by various means to demonstrate that the CP is solubilized efficiently by 1% Triton X-100 alone (CPE requires 1 M NaCl) and not by pH 9.0 (which releases CPE activity).

In addition, to demonstrate that the enzyme is a metallocarboxypeptidase, inhibition and activation studies are performed as follows. Diisopropylfluorophosphate (DFP), trans-epoxysuccinyl-L-leucylamido-(4-guanidino) butane (E64), and leupeptin should not inhibit CP activity while o-phenanthroline and D-L-2-mercaptomethyl-3-guanidinoethylthiopropanoic acid (MGTA) should completely inhibit CP activity (Song and Fricker, 1996, J. Biol. Chem. 271:28884–28889). Ten $\mu$M p-chloromercuriphenylsulfonate (PCMS) inhibits CPE activity by 90% but has little effect on CPD. For activation studies, 1 mm $CoCl_2$ has been reported to activate fibroblast membrane CPD activity by four-fold (McGwire et al., 1997, Life Sci. 60:715–724). All inhibitors and activators are used at levels previously published for CPD in McGwire et al., supra. Without wishing to be bound by theory, it is expected that CP activity is membrane-bound, has a low pH optimum, and is relatively insensitive to inhibition by PCMS. Carboxypeptidase B and carboxypeptidase N are soluble proteins with neutral pH optimum, CPM is membrane-bound, but has a neutral pH optimum.

EXAMPLE 3
Immunolocalization of Pigeon gp180 in Cells

The experiments presented in this example may be summarized as follows.

Antibodies to pigeon gp180 protein are prepared and are used to localize the protein in and on the surface of pigeon SMCs.

The Materials and Methods used in and the Results of the experiments presented in this example are now described.

Antibodies to gp180

Two rabbits are immunized with 100 $\mu$g each of antigen (i.e., the recombinant gp180 purified from COS cells) emulsified with complete Freund's adjuvant. After three weeks, the rabbits are given a second, booster injection of antigen with incomplete Freund's adjuvant. Subsequent booster injections are administered every 4–6 weeks using antigen with incomplete Freund's adjuvant. The rabbits are bled from a marginal ear vein every 7–14 days following each booster injection.

The antiserum collected is affinity purified using immunoblots as described in McGwire et al. (1997, Life Sci. 60:715–724). Briefly, the recombinant protein is loaded onto a large, preparative SDS-polyacrylamide gel which is then trans-blotted onto a PVDF membrane and probed with the antiserum. A strip is cut from one side of the membrane and the strip is used to detect the location of the bound antibodies by immunostaining. Once the location of the antibodies is determined, the antibody is eluted from the unstained remainder of the membrane by incubating the excised horizontal strip containing the bound antibodies in 100 mm glycine, pH 2.5, for 10 minutes. The buffer containing the eluted antibodies is removed and is neutralized with a one-tenth volume of 1 M Tris, pH 8.0, to elute the glycine. The specificity of the antibodies is determined against both native and denatured gp180 and CPE as a control, to ensure that the antibodies are specific for gp180 and/or CPD and do not cross-react with other non-specific proteins. The antibodies are then diluted for use to detect surface staining of gp180 on WC and SR SMCs.

Immunohistochemical Studies Localizing gp180

WC and SR SMCs are cultured on glass slides and used at logarithmic growth (proliferative state) and at confluence to detect the presence of gp180 using antibodies raised against gp180. Further, immunostaining of SMCs with anti-gp180 after HS downregulation of gp180 gene expression is also performed. Indirect immunostaining is performed using an avidin-peroxidase technique (Vectastain ABC Kit, Vector Labs., Inc., Burlingame, Calif.) per the manufacturer's instructions, with hematoxylin staining of nuclei as a counterstain as previously described elsewhere herein. Specific staining patterns and intensity of staining under various conditions is assessed.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of regulating nucleic acid expression in a cell wherein said nucleic acid is selected from the group consisting of a nucleic acid encoding a glycoprotein 180 polypeptide, and a nucleic acid encoding a carboxypeptidase protein, said method comprising contacting a eukaryotic cell with a nucleic acid-expression regulating amount of heparan sulfate, or a biological equivalent thereof, thereby regulating nucleic acid expression in said cell.

2. The method of claim 1, wherein said regulation is inhibition of nucleic acid expression.

3. The method of claim 1, wherein said glycoprotein 180 protein is selected from the group consisting of an avian gp180, and a rodent gp180.

4. The method of claim 1, wherein said carboxypeptidase protein is selected from the group consisting of a bovine carboxypeptidase D, a non-human primate carboxypeptidase D, and a human carboxypeptidase D.

5. A method of regulating nucleic acid expression in a cell, wherein said nucleic acid encodes a cell receptor protein, said method comprising contacting a eukaryotic cell with a nucleic acid-expression regulating amount of heparan sulfate, or a biological equivalent thereof, thereby regulating nucleic acid expression in said cell.

6. The method of claim 5, wherein said regulation is inhibition of nucleic acid expression.

7. The method of claim 6, wherein said cell receptor protein is selected from the group consisting of a glycoprotein 180, a carboxypeptidase protein, and a carboxypeptidase-like protein.

8. The method of claim 7, wherein said cell receptor protein is selected from the group consisting of an avian gp180, a rodent gp180, a bovine carboxypeptidase D, a non-human primate carboxypeptidase D, and a human carboxypeptidase D.

9. A method of regulating expression of a cell receptor protein, said method comprising contacting a eukaryotic cell with a nucleic acid-expression regulating amount of heparan sulfate, or a biological equivalent thereof, thereby regulating expression of a cell receptor protein.

10. The method of claim 9, wherein said cell receptor protein is a cell surface receptor protein.

11. The method of claim 10, wherein said cell receptor protein is selected from the group consisting of a glycoprotein 180, a carboxypeptidase protein, and a carboxypeptidase-like protein.

12. The method of claim 11, wherein said cell receptor protein is selected from the group consisting of an avian gp180, a rodent gp180, a bovine carboxypeptidase D, a non-human primate carboxypeptidase D, and a human carboxypeptidase D.

13. A method of reducing the level of carboxypeptidase activity in a cell, said method comprising contacting a cell comprising carboxypeptidase activity with a nucleic acid-expression inhibiting amount of heparan sulfate, or a biological equivalent thereof, wherein said heparan sulfate, or said biological equivalent thereof, reduces the level of expression of carboxypeptidase in said cell, thereby reducing the level of carboxypeptidase activity in a cell.

* * * * *